United States Patent
Kraus et al.

(10) Patent No.: US 8,357,122 B2
(45) Date of Patent: *Jan. 22, 2013

(54) VALVED INTRODUCER ASSEMBLY AND METHOD THEREFOR

(75) Inventors: Mark C. Kraus, Independence, MN (US); Grant A. Mauch, Delano, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/174,863

(22) Filed: Jul. 1, 2011

(65) Prior Publication Data

US 2011/0264047 A1    Oct. 27, 2011

Related U.S. Application Data

(63) Continuation of application No. 11/198,871, filed on Aug. 5, 2005, now Pat. No. 7,972,307.

(60) Provisional application No. 60/598,999, filed on Aug. 5, 2004.

(51) Int. Cl.
*A61M 5/178* (2006.01)
*A61M 5/00* (2006.01)

(52) U.S. Cl. ......... 604/164.01; 604/167.06; 604/167.03; 604/246

(58) Field of Classification Search .................. 604/244, 604/246–248, 164.01, 167.01–167.06; 606/108
See application file for complete search history.

(56) References Cited

U.S. PATENT DOCUMENTS

| 4,240,411 A | 12/1980 | Hosono |
| 4,424,833 A | 1/1984 | Spector et al. |
| 5,397,311 A | 3/1995 | Walker et al. |
| 5,779,697 A | 7/1998 | Glowa et al. |
| 6,024,729 A | 2/2000 | Dehdashtian et al. |
| 6,712,791 B2 | 3/2004 | Lui et al. |
| 2002/0035347 A1 | 3/2002 | Bagaoisan et al. |
| 2003/0050604 A1 | 3/2003 | Lui et al. |

*Primary Examiner* — Nicholas Lucchesi
*Assistant Examiner* — Rebecca E Eisenberg
(74) *Attorney, Agent, or Firm* — Michael F. Scalise

(57) ABSTRACT

An introducer assembly includes a sheath having a sheath proximal end and distal end, and a passage therethrough. The introducer assembly further includes a valve assembly that is sealingly associated with the passage of the sheath. The valve assembly includes a valve having a first seal and a second seal, where the first and second seal optionally have different sealing properties. For example, the first seal and the second seal have different thicknesses, different sealing durometers, or otherwise different sealing features. In another option, the sheath is removable from the instrument disposed therethrough. In yet another option, the valve of the valve assembly further includes a chamber disposed between the first and second seals. The seals are spaced to accommodate devices with multiple flow holes therein.

9 Claims, 14 Drawing Sheets

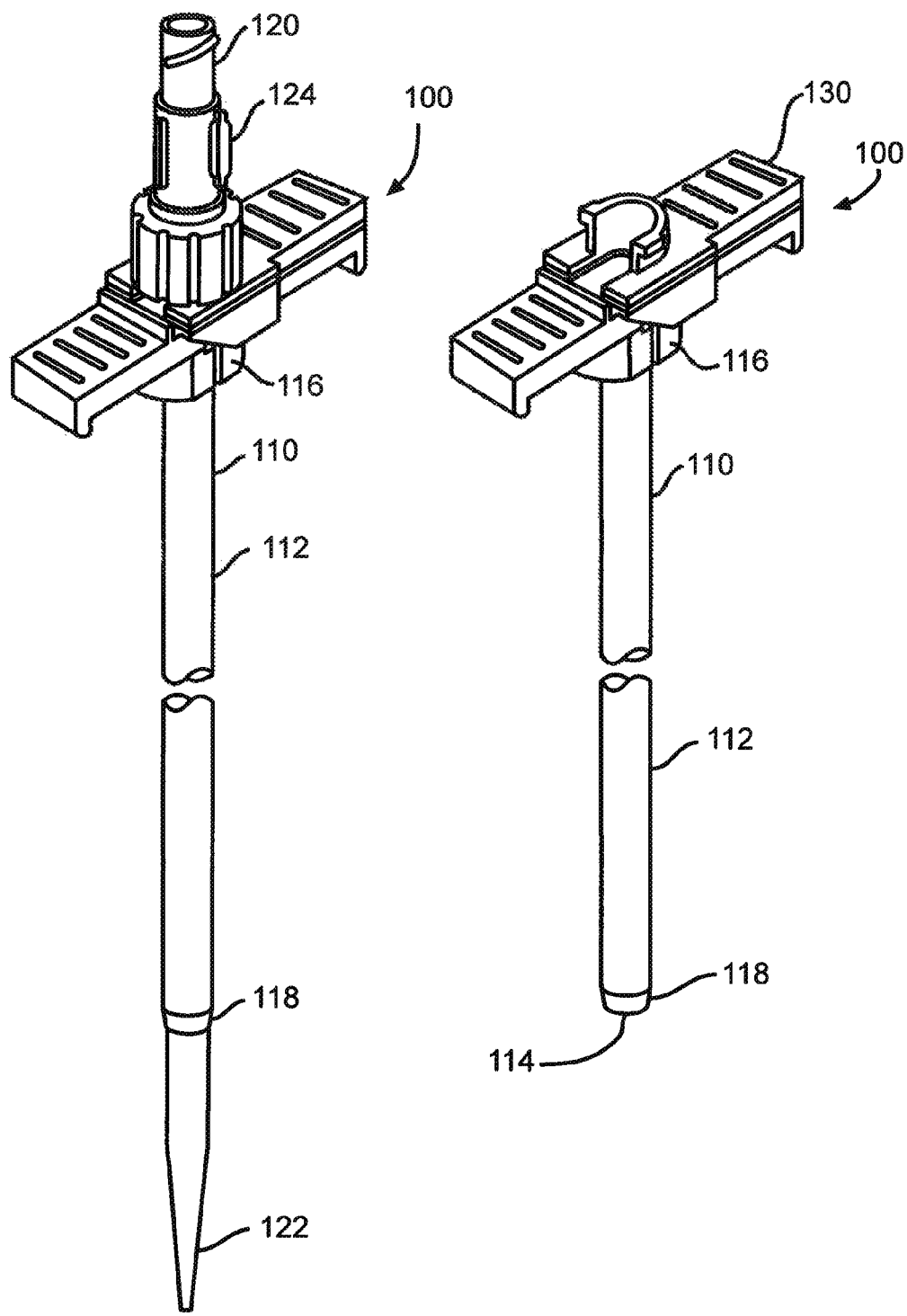

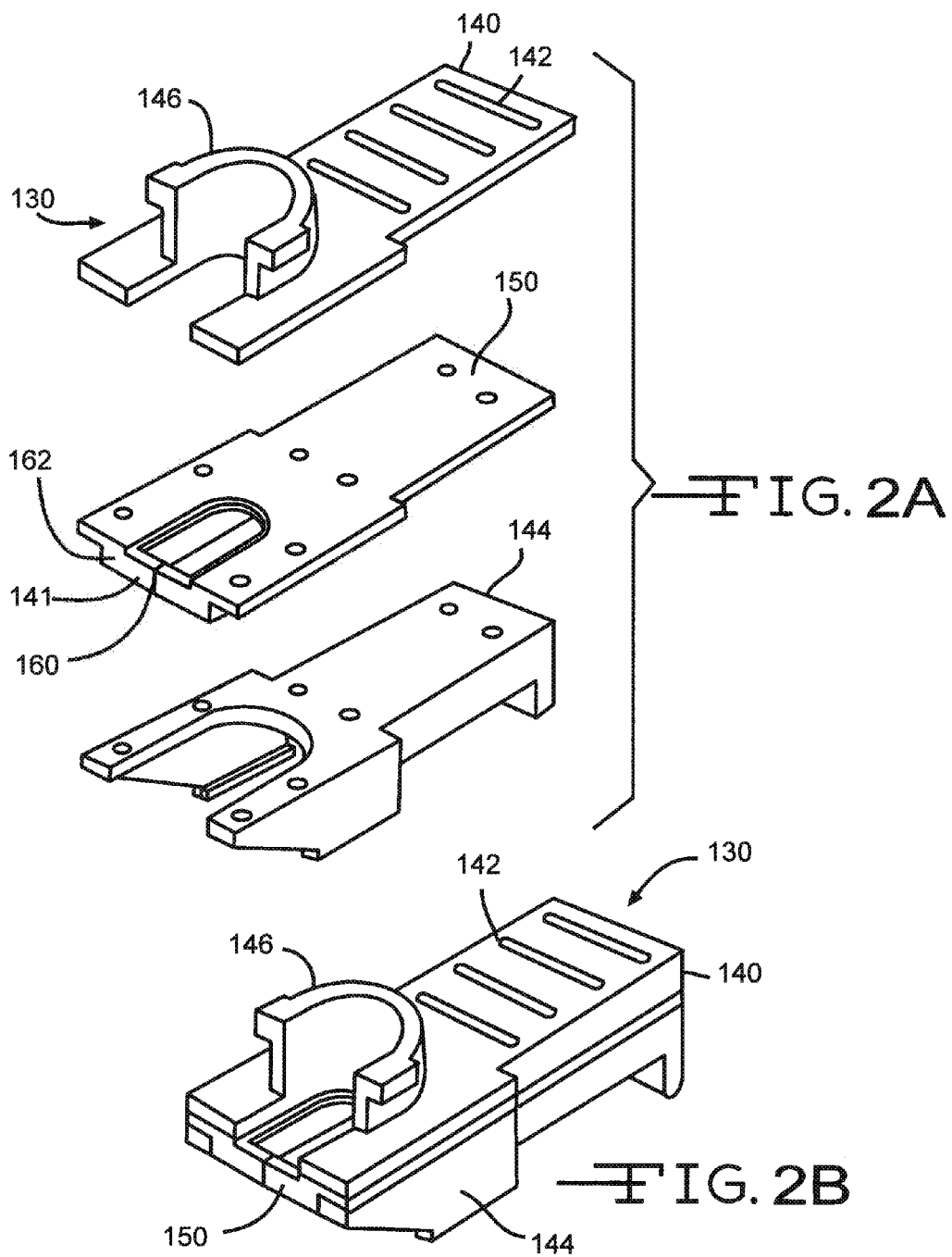

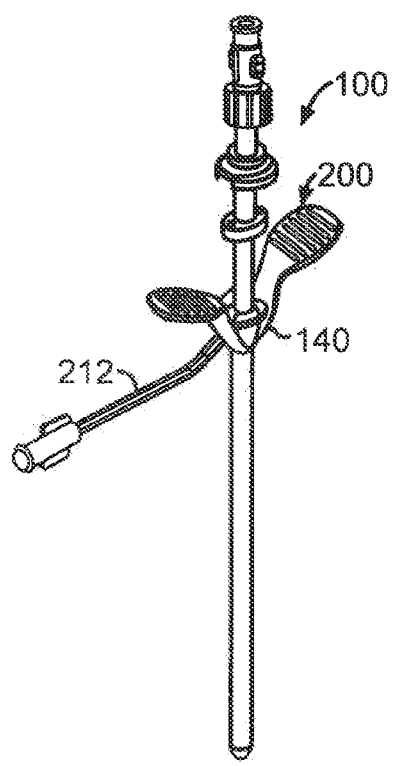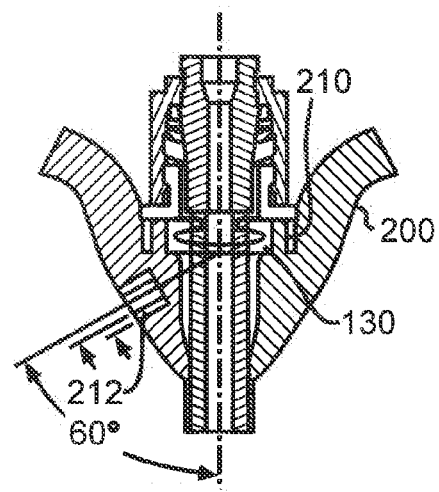
FIG. 11C
FIG. 11D

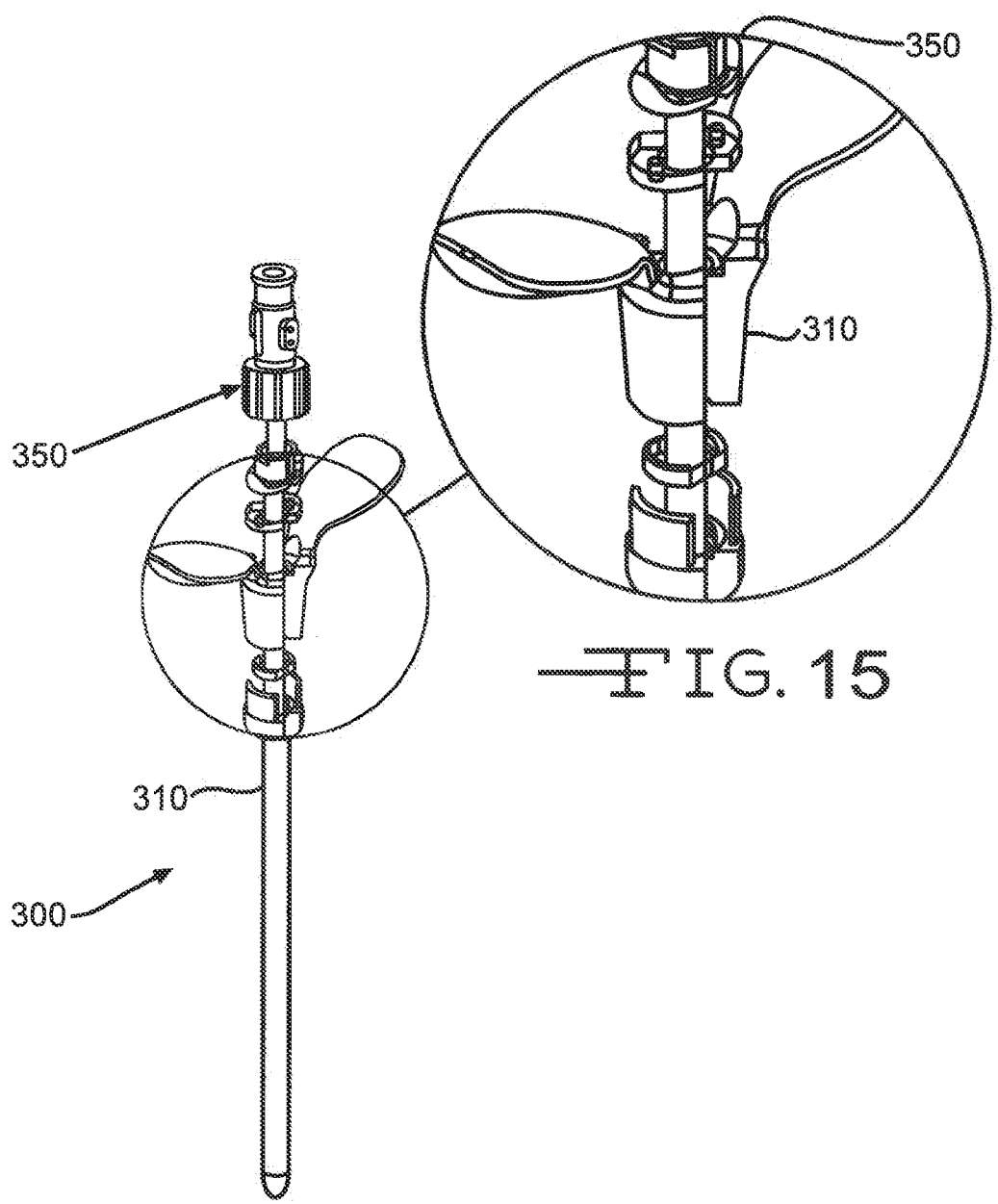

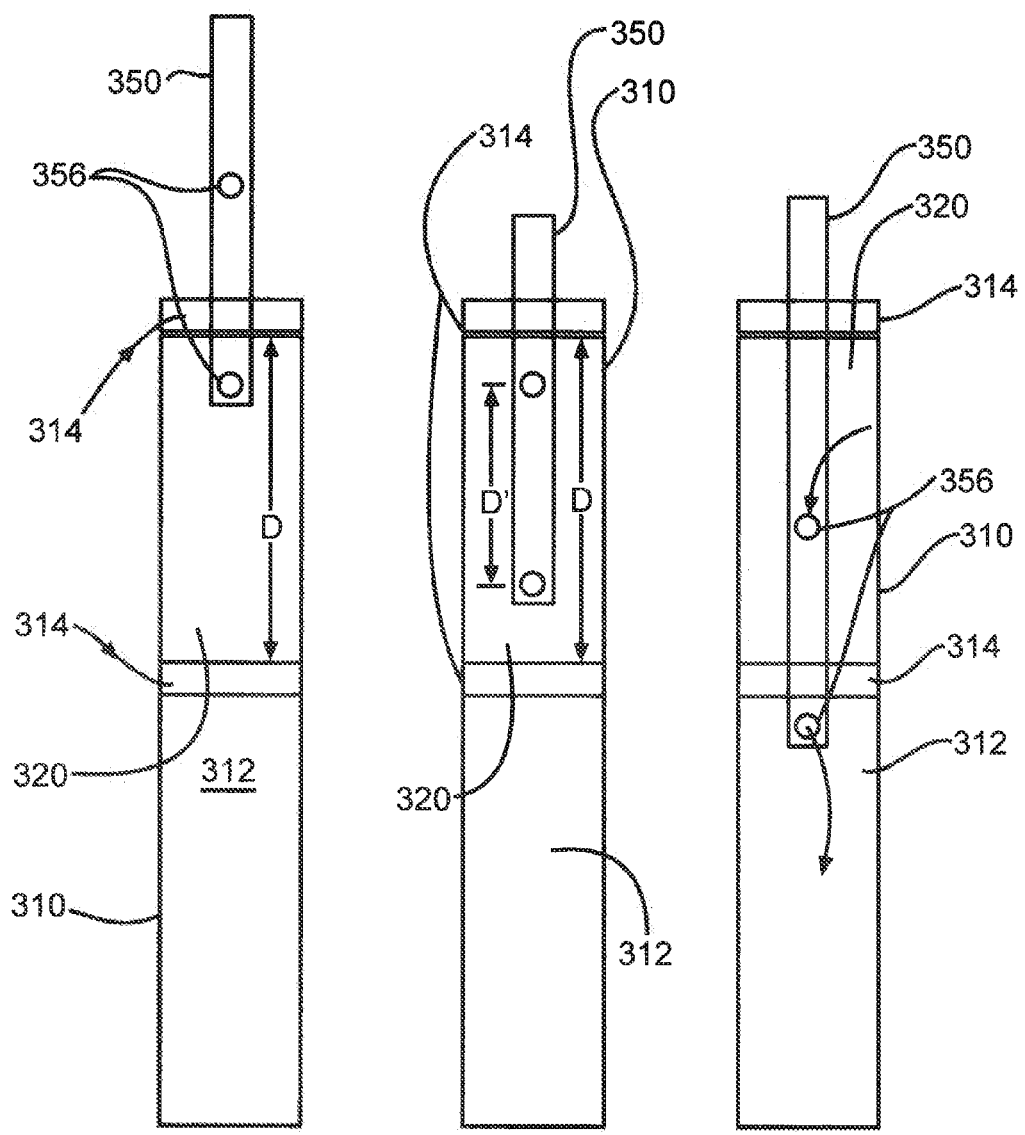

VALVED INTRODUCER ASSEMBLY AND METHOD THEREFOR

RELATED APPLICATION

This application is a continuation of U.S. patent application Ser. No. 11/198,871, filed Aug. 5, 2005, now U.S. Pat. No. 7,972,307 to Kraus et al., which claims priority under 35 U.S.C. 119(e) to U.S. Provisional Patent Application No. 60/598,999, filed Aug. 5, 2004, which applications are incorporated herein by reference and made a part hereof.

TECHNICAL FIELD

Introducers and introducing assemblies, and more specifically a valved introducer assembly and method.

BACKGROUND

Introducer devices provide for access to the venous system and are employed for inserting medical devices such as catheters, guidewires, leads, infusion ports, dialysis ports, dialysis catheters, and others. A typical procedure for gaining access to the central venous system or the arterial system with an introducer is the Seldinger Introduction Method. The Seldinger Method provides for insertion of a needle into the vasculature of a patient. Once the needle is in the vessel, the physician aspirates the needle to assure that the needle is in the vessel, and to draw out air present in the bore of the needle. The syringe is removed and discarded. A guide wire is inserted through the needle, and the needle is removed over the guide wire. The introducer, which includes a dilator and the sheath, is placed over the guidewire and inserted into the vessel. With the introducer and wire guide in the vessel, the dilator and wire guide are removed leaving only the sheath in the vessel. The desired medical device is implanted through the passage of the sheath. The sheath is optionally removed from the medical device. The introducer device provides access to the vein or artery, and therefore control of bleeding and the intake of air is necessary, for example, through use of a valve.

The introducer devices are designed to be used with both large and small instruments, such as dilators and guidewires. However, it can be difficult to effectively seal against instruments over such a wide variety of diameters. Furthermore, seals which are effective against larger diameter instruments are often ineffective in allowing smaller, or relatively softer devices, or devices having relatively lower column strength to pass through the seal. In addition, devices which have fragile features may be difficult to transfer through the seal without damage to the features and/or device.

Accordingly, what is needed is an introducer assembly which can effectively seal against a wide variety of instruments without inhibiting the throughput of the instrument, or damaging the instrument. What is also needed is an introducer assembly which does not distract or interfere with the implantation process.

SUMMARY

An introducer assembly is provided herein. The introducer includes a sheath having a sheath proximal end and distal end, and a passage therethrough. The introducer assembly further includes a valve assembly that is sealingly associated with the passage of this sheath. The valve assembly includes a valve having a first seal and a second seal, where the first and second seal optionally have different sealing properties. For example, the first seal and the second seal have different thicknesses, different sealing hardness qualities, or otherwise different sealing features. In another option, the sheath is removable from the instrument disposed therethrough. In yet another option, the valve of the valve assembly further includes a chamber disposed between the first and second seals, where the chamber includes a side exit that can optionally be sealingly closed. The sealing thickness, chamber thickness or diameter, or the dilator outer diameter can be modified as further discussed below.

During use of the device, a method includes disposing an instrument through an introducer, for example, the introducer having the qualities discussed above. For example, the introducer has a sheath extending from a sheath proximal end to a sheath distal end, and the sheath has a passage therethrough. The introducer further includes a valve assembly that is sealingly associated with the passage. The method further includes sealing a valve of the valve assembly against the instrument, where the valve includes at least a first seal on a second seal and optionally a chamber disposed between the first and second seals. The first seal may have one or more first properties which are different than the second seal which has one or more second properties. For example, the first and second seals have different thicknesses, and/or different hardnesses.

Advantageously, the introducer assembly described above provides many benefits. For example, the introducer assembly allows for a removable introducer assembly to seal against very soft instruments such as soft tipped leads or soft and delicate instruments. Another benefit is that the introducer allows for passing instruments through a seal with delicate features and/or tips through such sealing features, yet allowing for effective sealing against such devices. Examples of such delicate features include fasteners, electrodes, coatings, devices having low column strength, fiber optics, and lead attachment features such as tines or an active fixation device, such as a helix. Furthermore, the various features described above further allow for manufacturability of such a device and further allow for multiple seals having multiple different sealing properties to be incorporated with such a device.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 1A illustrates a perspective view of an introducing assembly as constructed in accordance with at least one embodiment;

FIG. 1B illustrates a perspective view of an introducing assembly as constructed in accordance with at least one embodiment;

FIG. 2A illustrates an exploded perspective view of a valve assembly as constructed in accordance with at least one embodiment;

FIG. 2B illustrates a perspective view of a valve assembly as constructed in accordance with at least one embodiment;

FIG. 11C illustrates a perspective view of an introducing assembly as constructed in accordance with at least one embodiment;

FIG. 11D illustrates a cross-sectional view of a portion of an introducing assembly as constructed in accordance with at least one embodiment;

FIG. 14 illustrates an exploded perspective view of an introducing assembly as constructed in accordance with at least one embodiment;

FIG. 15 illustrates an enlarged exploded perspective view of FIG. 14;

FIG. 17 illustrates a side elevational view of a portion of an introducing assembly with a medical instrument disposed therethrough;

FIG. 18 illustrates a side elevational view of a portion of an introducing assembly with a medical instrument disposed therethrough;

FIG. 19 illustrates a side elevational view of a portion of an introducing assembly with a medical instrument disposed therethrough.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1C:
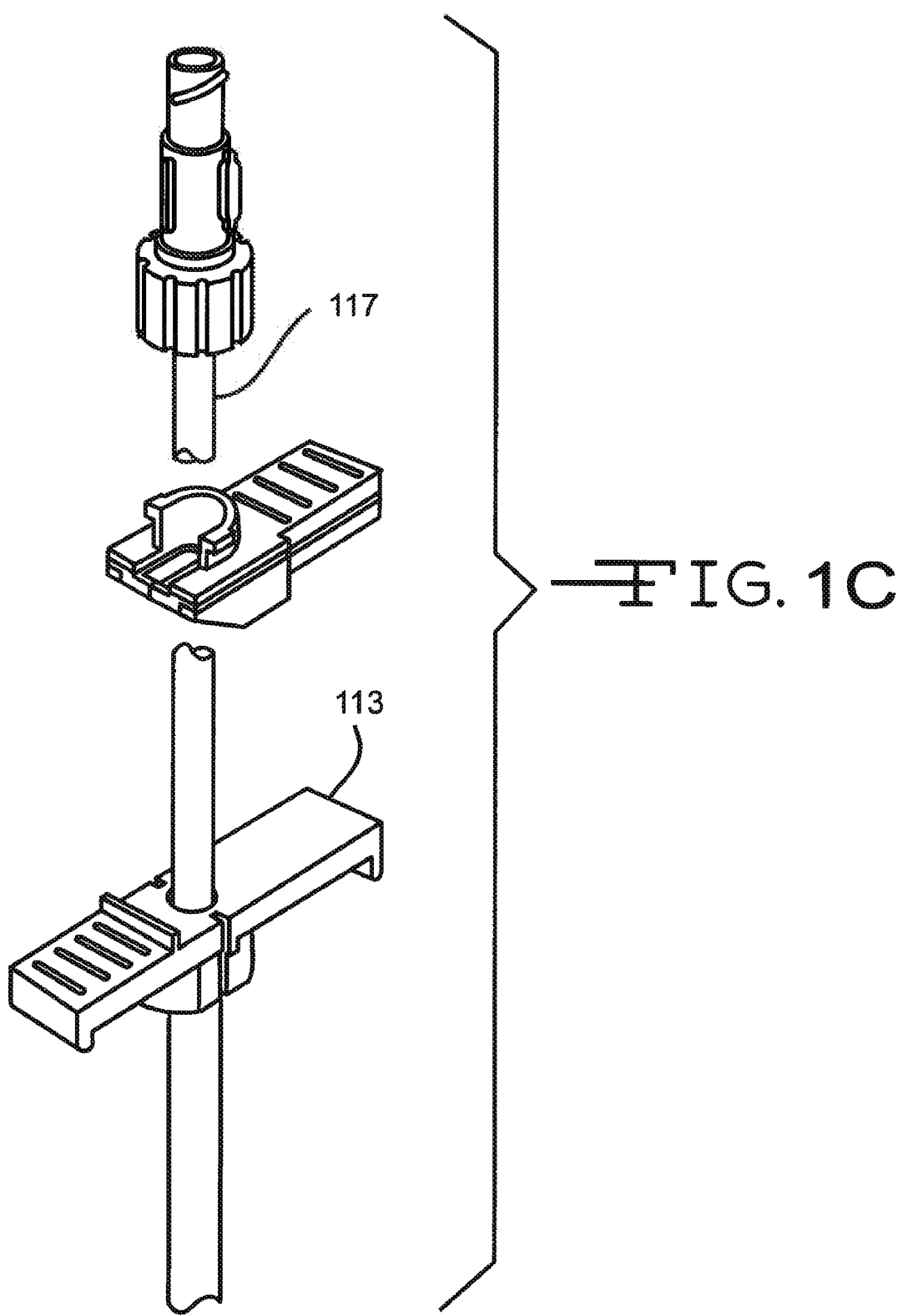
FIG. 1C illustrates a perspective view of an introducing assembly as constructed in accordance with at least one embodiment.

An introducer assembly 100 is illustrated in FIGS. 1A, 1B, and 1C. The introducer assembly includes an introducer 110 having a sheath 112 with a passage 114 therethrough. The sheath extends from a sheath proximal end 116 to a sheath distal end 118. Near the sheath distal end 118 is a tapered portion, allowing for a more tapered transition portion to taper to the dilator disposed therethrough.

The introducer assembly further includes an instrument such as a dilator 120 that is coupled with the introducer, for example, with a rotatable coupler. The dilator 120 is removably disposed within a passage of the sheath 112. The sheath 112 includes a support diameter 113 which is sized to receive a dilator 120 having a dilator diameter 117 therethrough. It should be noted that other instruments such as leads and/or guidewires can be disposed through the sheath and sheath passage 114, as will further be described below. The dilator 120 extends from a dilator distal end 122 to a dilator proximal end 124, where the dilator distal end 122 is insertable into a patient, for example, over a needle or a guidewire. The dilator distal end 122 optionally ends in a tapered end, allowing for ease of transition within tissue of a patient. The dilator proximal end 124 optionally includes features, such as a luer hub or threads, that allows for other devices to be coupled thereto.

Referring again to the sheath 112, the sheath 112 includes various types of sheaths, for instance, the sheath 112 can comprise a sheath which has a strengthening material, such as a strengthening braid of material. Alternatively, the sheath 112 includes a sheath which is modified to assist in preventing bends and/or kinks along the sheath. The sheath 112 is defined in part by a longitudinal axis, and the sheath 112 is, in one option, coaxial with the dilator 120.

In one embodiment, the introducer 110 and the sheath 112 are removable from around instruments disposed therein, such as a lead disposed with the sheath 112. For example, the sheath 112 is removable from around the instrument without having to slide or otherwise manipulate the introducer and/or the sheath over a proximal end of the instrument. In one option, the introducer and/or sheath are removed from an outer perimeter along a cross-section of an instrument disposed therethrough.

The sheath 112, for example, can be removed from the instrument disposed therethrough in a number of different manners. For example, the sheath 112 can include structure integral therewith or non-integral that allows for the sheath to be separated from around the instrument without damaging the instrument, and/or allows for the sheath to be removed from the outer perimeter of the cross-section of the instrument. In some non-limiting examples, the structure includes one or more tabs that are connected with the sheath to tear the sheath off of the instrument. In another example, the structure includes a tear strip, molecularly orientated material within the sheath, one or more openings in the sheath allowing the sheath to separate at one or more locations that each can be used alone or in combination to separate the sheath from around the instrument. In another option, the sheath is at least partially dissolvable within a body, allowing the sheath to be removed from the instrument. In another option, a slitting or splitting device such as a slitter can be used to removed the sheath, where the sheath is removed by slitting. In yet another option, the sheath further includes one, two or more tabs which can be used to separate the sheath away from the instrument. Further options include a pre-weakened or scored sheath, allowing for the sheath to be manually removed by tearing, separating, or slitting, for example. In yet another example, the sheath includes molecularly oriented material allowing for the sheath to be removed from around the instrument.

The introducer assembly 100 further includes a valve assembly 130 which is sealingly associated with the passage of the sheath, allowing for substantial sealing of the passage preventing fluids to exit from a patient when the sheath is disposed within the patient. The valve assembly 130 assists in preventing fluids from exiting, yet permits passage of instruments through the valve assembly 130, and substantially seals against the instruments that are disposed therethrough. The valve assembly 130, as further described below, allows for sealing against instruments that have a wide variety of diameters, and/or features, or soft tipped devices.

The valve assembly 130 is coupled with a portion of the introducer 110, for example, along one or more tabs of the introducer. The valve assembly 130 is removable from around an outer cross-sectional perimeter of an instrument disposed through the introducer, similar to the manner suggested above for the introducer and/or sheath. In one option, the valve assembly has a U-shaped housing structure, where it has an open end on its housing such that it can be removed a way from an instrument without having to split apart the valve assembly. In another option, a valve membrane of the valve assembly 130 includes tear away features, allowing for the valve membrane to be removed from instruments disposed therein. The valve of the valve assembly 130 further allows for the valve assembly 130 to be removed from around an instrument, as further described below.

The valve assembly 130, as shown in more detail in FIGS. 2A and 2B includes a housing 140 which provides support to the valve assembly 130. The housing 140, in one option, is secured along a portion of the introducer 110 (FIG. 1B) that is offset from the introducer passage, and the housing 140 is cantilevered over the passage of the introducer.

In one option, the housing 140 includes a first housing portion 142 and a second housing portion 144 where a valve 150 for sealing the instruments 150 is disposed between the two portions 142 and 144. It should be noted that the housing 140 can alternatively includes only the first housing portion 142 or only the second housing portion 144, other housing combinations are suitable as well.

The first portion 142 of the housing 140 and a second portion 144 of the housing are disposed about the valve 150 forming a sandwich, where the first portion 142 is coupled with the second portion 144. Examples of ways in which the first portion 142 is coupled with the second portion 144 include, but are not limited to, ultrasonic welding, interference fit, snap-fit coupling, mechanical fasteners, adhesive, or compression fit. The housing 140, in one option, forms a U-shaped structure such that it can be removed from around instruments disposed therethrough without having to separate the housing 140. In another option, the housing 140 includes a hub structure 146 allowing for other devices, such as a dilator, to be coupled therewith. In one option, the structure 146 includes a luer hub with features such as those illustrated in FIG. 2A, which allows for another threaded component to be threadingly coupled therewith.

The valve assembly 130 is coupled with the introducer 110 (FIG. 1B), for example, along a tab of the introducer 110 (FIG. 1B). In one option, the housing 140 is wrapped around a portion of the introducer 110 (FIG. 1B), and optionally is snap-fittedly coupled with the introducer 110 (FIG. 1B). Alternatively, the valve assembly 130 can be made integral with the introducer 110 (FIG. 1B). In yet another option, the valve assembly 130 forms an adapter that is attachable and removable by the user before, during, or after an implant procedure. For example, the user can remove or attach the valve assembly 130 with a fitting or other coupling.

Figures 3, 4:
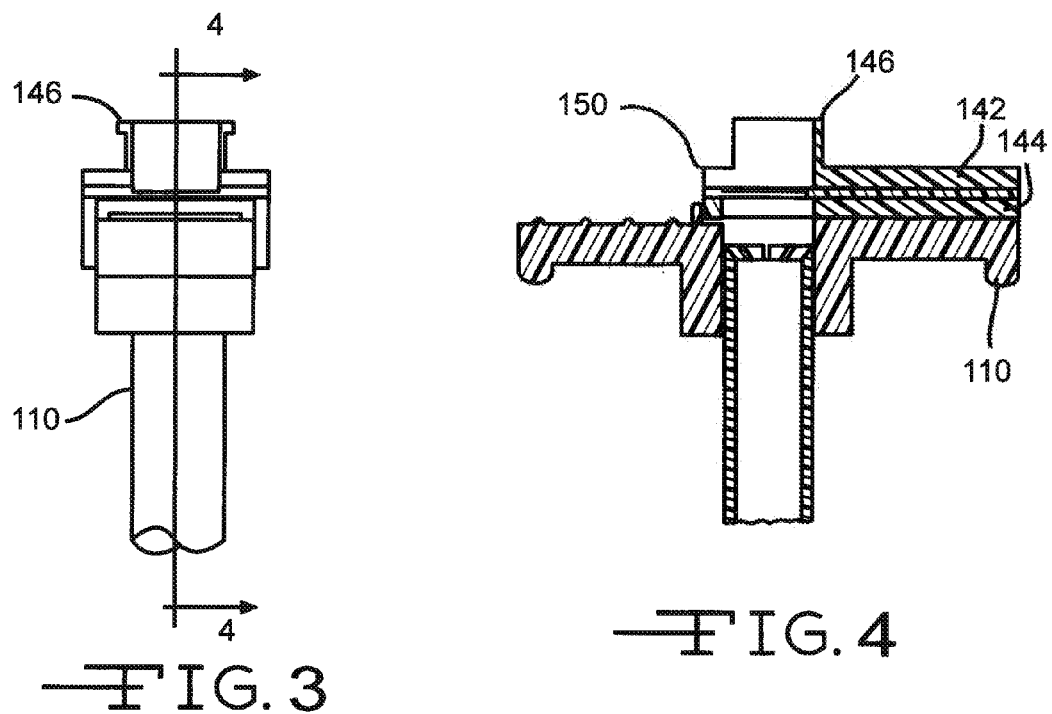
FIG. 3 illustrates a side elevational view of a portion of an introducing assembly as constructed in accordance with at least one embodiment.
FIG. 4 illustrates side cross-sectional view of a portion of an introducing assembly taken along 4-4.
Figure 5:
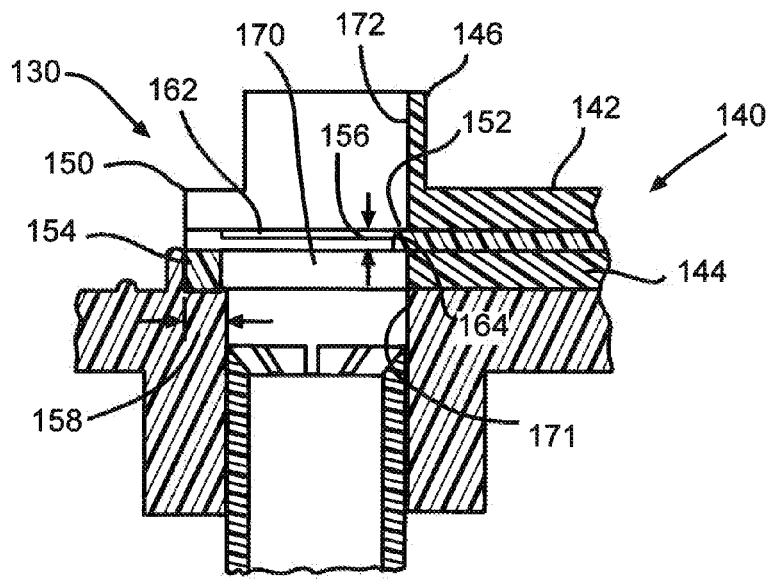
FIG. 5 illustrates side cross-sectional view of a portion of an introducing assembly as constructed in accordance with at least one embodiment.

FIGS. 3, 4 and 5 illustrate the valve assembly 130 in greater detail. The valve 150 includes multiple valves therein, for example, in one option, a first seal 152 and a second seal 154. The first seal 152 is defined by a first seal thickness 156, and the second seal 154 is defined in part by a second seal thickness 158. The first seal thickness 156, in one option, is lesser than the second seal thickness 158. In another option, the ratio of the first seal thickness 156 to the second seal thickness 158 includes, but is not limited to Table 1 (see below).

In one option, the first seal thickness 156 is approximately 0.020 inches (0.508 mm) or 0.040 inches (1.016 mm). The second valve thickness 158, in one option, is approximately 0.035 inches (0.889 mm). It should be noted that the first seal 152 and the second seal 154 can be further modified to provide different sealing properties to the instruments disposed therethrough. For instance, the first seal 152 and the second seal 154 have different sealing thicknesses, as listed in Table 1, and can be combined with other variations, such as material hardness properties.

Examples of Sealing Variables

TABLE 1

| | Examples | | | | | | | |
|---|---|---|---|---|---|---|---|---|
| | 1 | 2 | 3 | 4 | 5 | 6 | 7 | 8 |
| 1st Sealing Surface thickness (inches), 156 | 0.020 | 0.020 | 0.040 | 0.040 | 0.020 | 0.020 | 0.040 | 0.040 |
| 2nd Sealing Surface thickness (inches), 158 | 0.035 | 0.035 | 0.035 | 0.035 | 0.035 | 0.035 | 0.035 | 0.035 |
| Chamber thickness (inches), 171 | 0.050 | 0.070 | 0.050 | 0.070 | 0.050 | 0.070 | 0.050 | 0.070 |

TABLE 1-continued

| | Examples | | | | | | | |
|---|---|---|---|---|---|---|---|---|
| | 1 | 2 | 3 | 4 | 5 | 6 | 7 | 8 |
| 1st Seal Hardness (Shore A) 152 | 40 | 40 | 40 | 40 | 70 | 70 | 70 | 70 |
| 2nd Seal Hardness (Shore A) 158 | 40 | 40 | 40 | 40 | 70 | 70 | 70 | 70 |

In another option, the first and second seals 152, 154 have different sealing properties as the material properties, such as sealing hardness, where the sealing properties are different for the first and second seals 152 and 154. For example, in one option, the first seal has a durometer of approximately 20 or 30 Shore A hardness, and the second seal has a hardness of approximately 40 Shore A hardness. In another example, the first sealing hardness is about 40-70 Shore A. In another example, the second sealing hardness is about 40-70 Shore A. In an example, the first sealing hardness is different than the second sealing hardness. In another example, the first sealing hardness is lesser than the second sealing hardness. In yet another example, the first sealing hardness is greater than the second sealing hardness. Other examples and combinations of material hardnesses and/or seal/chamber thicknesses are listed in Table 1 above. Suitable materials for the first and/or second seals 152, 154 include, but are not limited to, silicone, thermoplastic rubbers (TPR), or thermoplastic urethane (TPU).

Figure 7A:
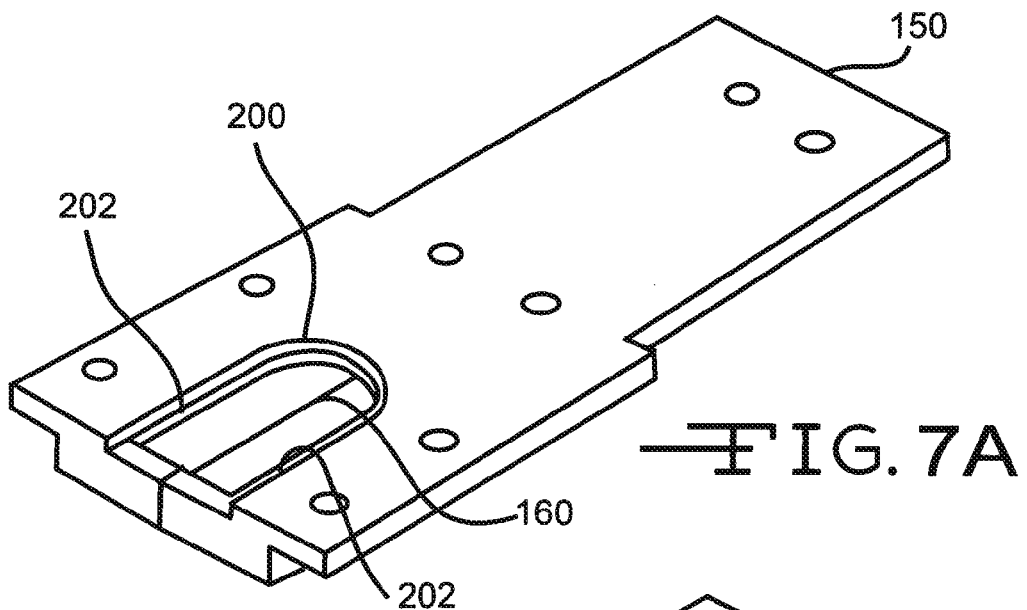
FIG. 7A illustrates a perspective view of a valve as constructed in accordance with at least one embodiment.
Figure 7B:
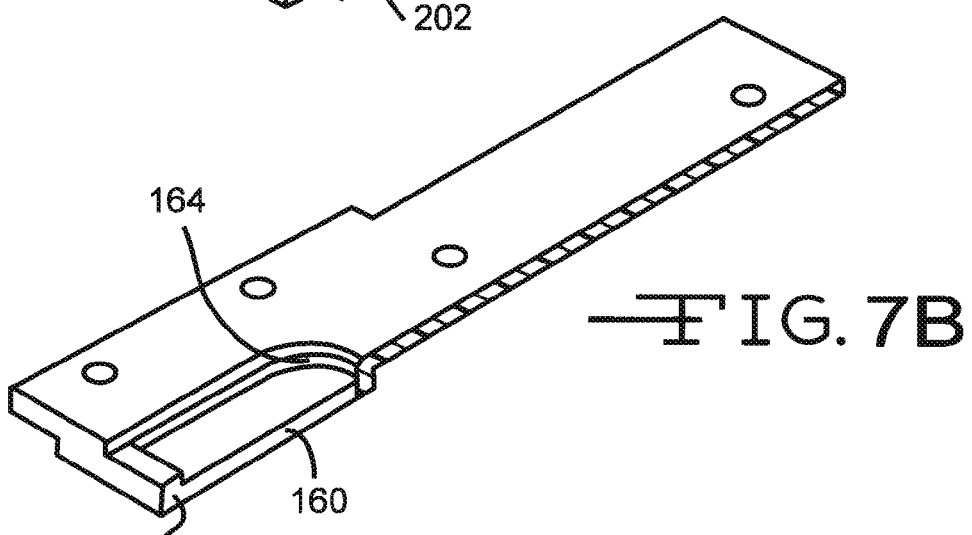
FIG. 7B illustrates a cross-sectional view of a portion of a valve assembly as constructed in accordance with at least one embodiment.
Figure 7C:
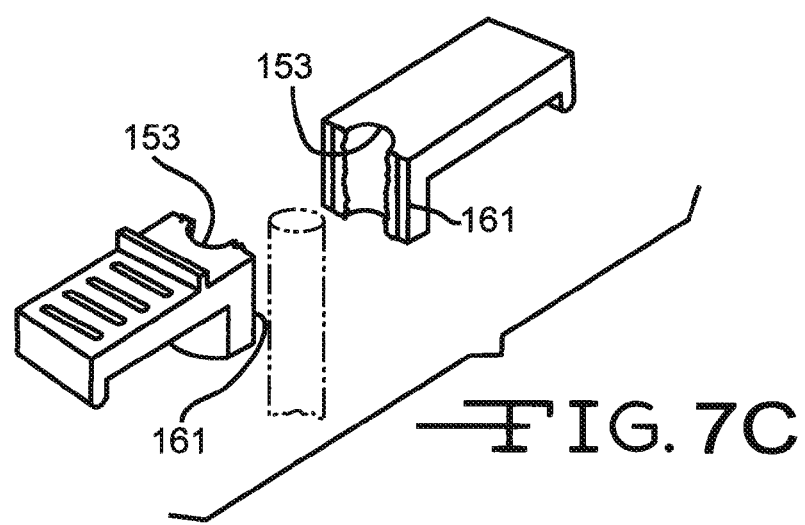
FIG. 7C illustrates a cross-sectional view of a portion of a valve assembly as constructed in accordance with at least one embodiment.

In yet another option, the first and/or second seals 152, 154 are provided with features that allow for the first and/or second seals 152 and 154 to be sealed against non-circular instruments, or non-circular instruments and/or circular instruments. The first and/or second seals 152, 154, in another option, have features that allow for sealing against multiple instruments disposed through the first and second seals 152, 154 simultaneously. In one option, the first seal 152 includes a single slit, or a plurality of slits 160, such as an asterisk pattern, as illustrated in FIG. 7A. The first seal 152 can include other shapes and sizes as well. For example, FIG. 7B illustrates an example where the first seal 152 has a circular opening shape 153. In another option, the second seal 154 has a single slit of material, and/or a plurality of slits. In another option, the first and second seals 152, 154 includes features such as the slits 160 that extend to the outer edge 141 (FIG. 2A) of the valve 150. This provides for a path for an instrument disposed therethrough to travel as the valve assembly is removed from around the instrument. Alternatively, in another option, at least one of the first or second seals 152, 154 include slits 160 that do not extend to the outer edge 141. For example, a web 161 of material is included near the outer edge 141, providing additional structural and/or sealing support for the valve assembly, as illustrated in FIG. 7C.

Referring to FIG. 5, the first seal 152, is formed for example, by a slit on the first outer surface 162 of the valve and the second seal 154 forms a slit structure on the second outer surface 164 of the valve, the slit structure extends through the valve from the first outer surface 162 to the second outer surface 164. In another option, as illustrated in FIG. 7B, a hole 153 is formed as the first seal 152, where the hole 153 optionally includes tapered features 155. Referring again to FIG. 5 or 7A, the slit structure, optionally, extends through the valve from the first outer surface 162 to the second outer surface 164, and extends from an intermediate portion to the outer edge 141 (FIG. 2A) of the valve 150. In another option, as illustrated in FIG. 7C, the slit structure of the first seal 152 extends through the first outer surface 162 to the second outer surface 164, but does not extend through edge 141.

The valve 150, in another option, includes a chamber 170 therein. The chamber 170, which in one option is non-symmetrical, is disposed between the first seal 152 and the second seal 154. In another example, the chamber 170 has an elliptical shape. The chamber 170 allows for the two sealing surfaces to be provided with one valve assembly, and further serves to provide back bleed prevention. The chamber further allows for the first and second seals 152 and 154 to be formed of two different sealing properties.

The chamber 170 is defined in part by a chamber thickness 171. The chamber thickness 171, in one option, is greater than the first sealing thickness and/or the second sealing thickness 158. Other variations for the chamber thickness 171, and the chamber thickness relative to the first and/or second sealing thickness 156, 158, are listed above in Table 1.

The chamber 170, in one option, has a side exit 172 where in an unassembled structure the side exit 172 has a slightly open structure position. The side exit 172 allows for the chamber 170 to be formed within valve assembly, while allowing for multiple different types of seals to be formed in the first and second seals 152 and 154. For example, the valve 150 can be molded into the shape illustrated in FIG. 5, where the insert for the chamber 170 can be removed during the molding process, and the slits can be formed by secondary operations.

Figure 6:
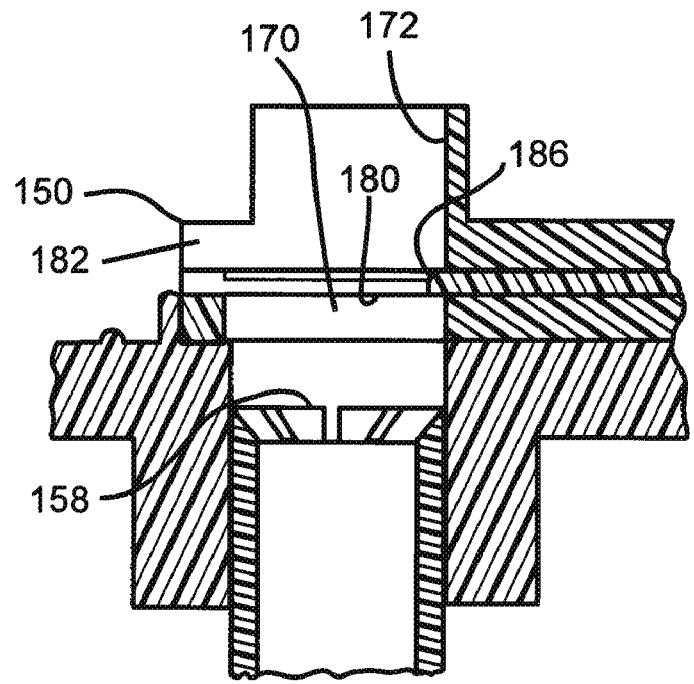
FIG. 6 illustrates a perspective view of a valve cross-section as constructed in accordance with at least one embodiment.

Referring to FIG. 6, the chamber 170 is defined in part by an upper surface 180, side surfaces 182 and a bottom surface 184. The side exit 172, in one option, as formed in one or more the side surfaces 182 of the chamber 170. In another option, the chamber 170 further includes a tapered portion 186, which allows for further manufacturability, for example, when removing an insert of the mold.

Figure 8:
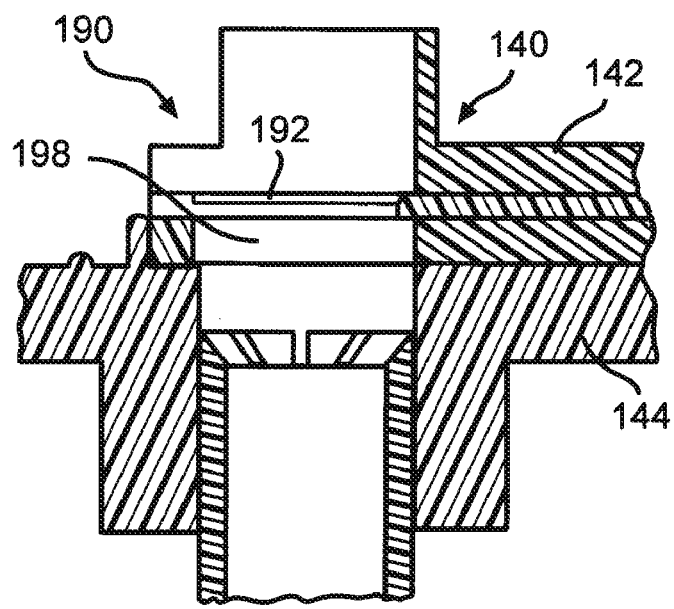
FIG. 8 illustrates a perspective view of a valve assembly cross-section as constructed in accordance with at least one embodiment.

The valve 150 optionally further includes structure 190 for sealing the chamber 170, as illustrated in FIG. 8. In one option, the structure includes a crush ring 192 that allows for an upper portion of the valve 150 to be sealingly engaged with a lower portion of the valve. In one option, the structure 190 includes a crush ring 192 that engages with a lower ring 198 of the valve 150. In another option, the crush ring 192 can be formed on upper and/or lower surfaces of the side exit. The structure 190 such as the crush ring allows for the chamber 170 to be effectively sealed during use. Furthermore, the crush ring features aid in manufacturability of the valve assembly.

In another option, the chamber 170 is sealed in other manners. For example, the chamber 170 can be bonded, for example, with adhesive, sealer, or filler. In another option, the valve 150 is formed of two separate pieces that are bonded together. In yet another option, the valve 150 is formed of two separate pieces that mate together, and are laminated together.

Referring to FIGS. 7 and 8, the valve 150 further includes a channel 200 with ramped portions 202 that allow for the housing 140 to compress the upper and lower portions of the valve 150 together, to seal the chamber within the valve. For example, a projection 204 of the housing 140 engages the ramped portion to compress the valve 150, and seal the chamber 170. When the first part 142 and the second part 144 of the housing 140 are coupled together, portions of the housing engage with the ramp 202 of the channel 200 of the valve 150, to compress and seal the chamber 170, as further shown in FIGS. 6, 7 and 8.

Figure 10:
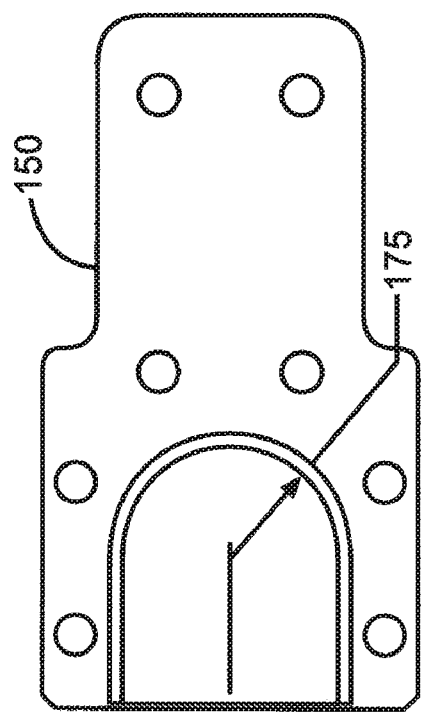
FIG. 10 illustrates a top view of a valve as constructed in accordance with at least one embodiment.
Figure 9:
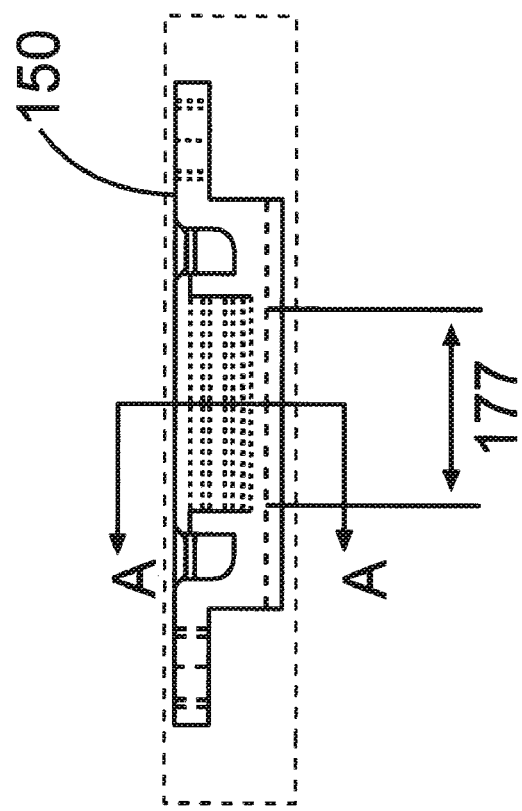
FIG. 9 illustrates an end view of a valve as constructed in accordance with at least one embodiment.

Further variations for the valve assembly include relative sizes for the valve minor diameter 175 and the chamber diameter 177, as illustrated in FIGS. 9 and 10. For example, Table 2 illustrates examples of relative dimensions for a dilator to be used with a sheath (see FIG. 1C), and the relative valve minor diameter 175, support diameter 113, and chamber diameter 177.

where the opening has an opening diameter. In an example, the opening diameters include, but are not limited to about 0.070 inches, 0.090 inches, or 0.120 inches. The circular opening allows for the valve assembly to seal against components disposed therethrough. Other structures for the first seal 152 are possible as discussed above, for example, including, but not limited to one or more slits.

The chamber 170 in an option, has an elliptical shape and has a width 157. The width dimensions include, but are not limited to, 0.215 inches, 0.270 inches, or 0.310 inches. The chamber can have other shapes and cross sections, including, but not limited to circular, square, or rectangular shapes, or those discussed above.

Figure 11A:
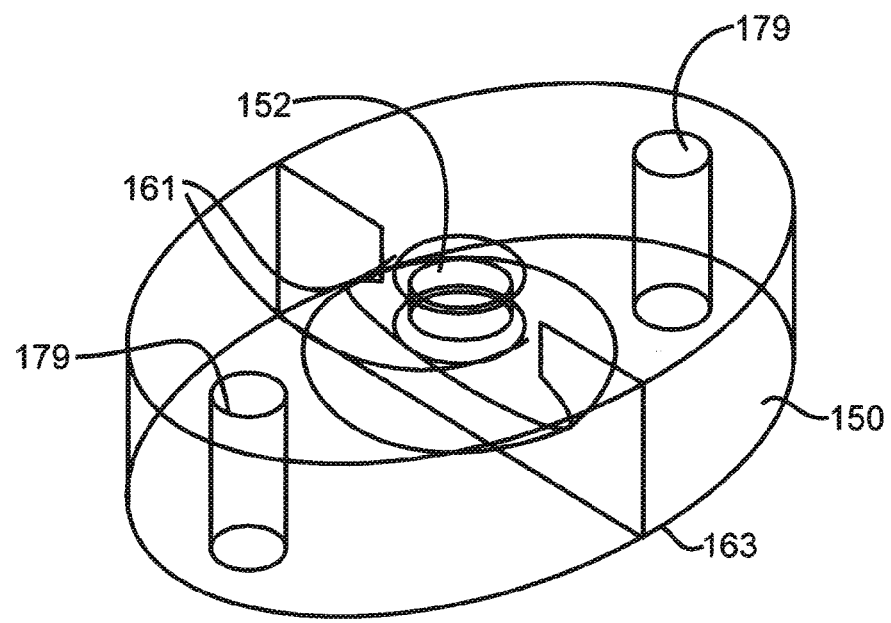
FIG. 11A illustrates a perspective view of a valve as constructed in accordance with at least one embodiment.
Figure 11B:
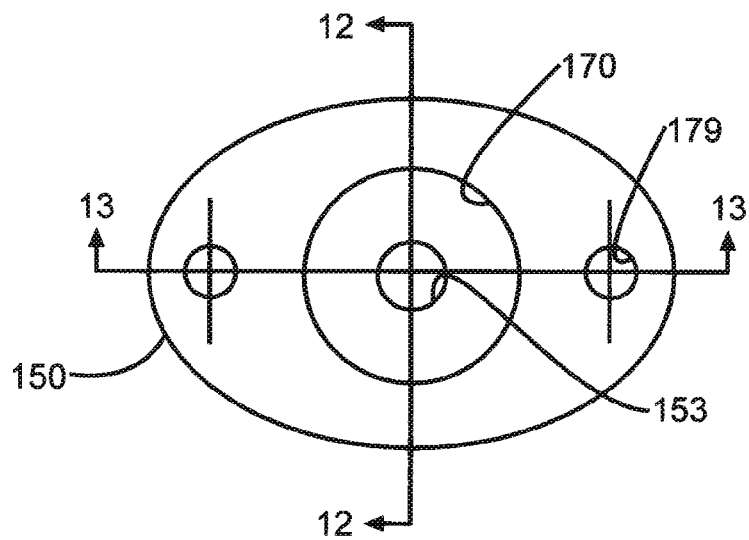
FIG. 11B illustrates a top view of a valve as constructed in accordance with at least one embodiment.
Figure 12:
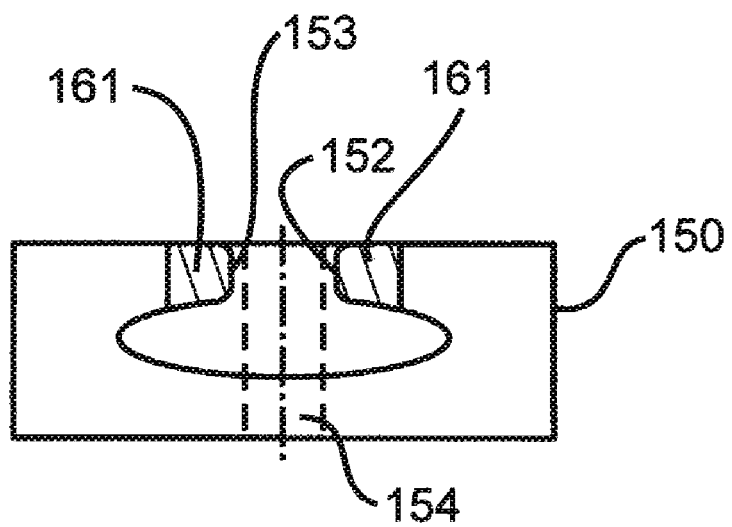
FIG. 12 illustrates a cross-sectional view of a valve taken along 12-12 of FIG. 11B.
Figure 13:
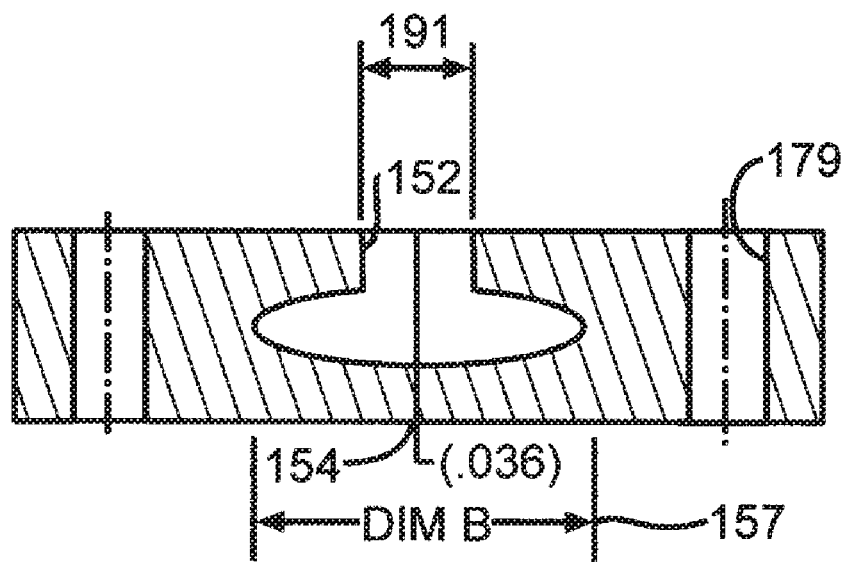
FIG. 13 illustrates a cross-sectional view of a valve taken along 13-13 of FIG. 11B.

The second seal 154 provides a second sealing surface for components disposed therethrough. In an example, the second seal 154 includes a slitted portion 163. In an example, the slitted portion 163 extends partially through the valve 150. In another example, the slitted portion 163 extends through the entire valve 150, as illustrated in FIG. 11A. In another example, a web 161 of material is disposed between the slitted portion 163 and the first seal 152. The web 161, in one embodiment, is sized to allow for the valve 150 to be torn as the introducer is removed or torn apart. The valve 150

Assembly Dimensions

TABLE 2

| Dilator Ø (Fr/inches) | Support Ø 113 (Fr/inches) | Valve Minor Ø 175 (inches) | Chamber Ø 177 (inches) | Ratio 1 Dilator Ø % of Valve Minor Ø | Ratio 2 Dilator Ø % of Valve Chamber Ø | Ratio 3 Dilator Ø % of Valve Support Ø |
|---|---|---|---|---|---|---|
| 7FR  0.092 | 7FR  0.173 | 0.179 | 0.174 | 51% | 53% | 53% |
| 8FR  0.111 | 8FR  0.192 | 0.179 | 0.174 | 62% | 64% | 58% |
| 9FR  0.118 | 9FR  0.199 | 0.179 | 0.174 | 66% | 68% | 59% |
| 10FR 0.137 | 10FR 0.218 | 0.179 | 0.174 | 77% | 79% | 63% |
| 11FR 0.145 | 11FR 0.226 | 0.179 | 0.174 | 81% | 83% | 64% |
| 12FR 0.158 | 12FR 0.239 | 0.179 | 0.174 | 88% | 91% | 66% |

FIGS. 11A, 11B, 11C, 11D, 12, and 13 illustrate another embodiment for the introducer or valve. FIG. 11C illustrates an introducer assembly 100 and a dilator disposed therethrough. The introducer assembly 100 includes a handle assembly 200 that houses a valve assembly 130 therein, and for example, forms a housing 140 for the valve assembly. The handle assembly 200 includes separable tabs used to tear away the valve assembly 130, for example, when a component such as a dilator is disposed within the sheath. Other methods or structures can be used to separate or otherwise remove the introducer from components disposed therethrough. A side port assembly 212 is coupled with the handle assembly 200 and allows for the valve assembly 130 to be flushed with fluid, such as saline. The side port assembly 212 further allows for medicine to be introduced therein. The handle assembly 200 further includes structure that couples with the valve assembly, and further allows for the valve assembly 130 to be removed. For example, the handle assembly 200 includes one or more posts 210 that are received within a portion of the valve assembly 130, as illustrated in FIG. 11D.

The valve assembly 130 is further shown in FIGS. 11A, 11B, 12, and 13. The valve assembly 130 includes a valve 150 having multiple sealing structures. For example, the valve 150 includes two or more sealing structures, such as a first seal 152 and a second seal 154. The first and second seals form a chamber 170 therebetween. In an example, the first seal 152 includes a opening 153 such as a circular opening, includes additional structure allowing for the valve 150 to be separated or torn away from components therethrough. For example, the valve 150 optionally further includes one or more post openings 179 that receive posts 210 (FIG. 11D) therein. As the handle assembly 200 (FIG. 11D) is separated, the posts 210 (FIG. 11D) assist in separating the valve 150. FIGS. 20A-20E illustrate further examples of slit configurations for valve 150. The seals have respective seal thicknesses, and the chamber has a chamber thickness. Furthermore, medical instruments, such as dilators, have an outer diameter. The ratios of the relative seal thicknesses, and chamber thickness, and seal properties include, but are not limited to, those shown in Tables 1 and 3 above and below. The first seal, in an option, includes a hole having a hole diameter 191. The hole diameter 191 can include the diameters, and relative diameters shown in Table 3. Furthermore, in an example, a sum of the hole diameter 191, the first sealing thickness, and the second sealing thickness is less than two times an outer diameter of a medical instrument disposed through the sheath. Further examples include a hole having a stretch listed in Table 3. Other examples include a hole having a stretch of about 30-60%, or a hole having a stretch of about 20-50%. One example of calculating the hole stretch is (Dilator O.D.−Valve Hole Ø)/Valve Hole Ø). In another example, in a valve having a first seal, a second seal, and a chamber therebetween, the sum of the first seal and the second seal is less than an outer diameter of the dilator.

EXAMPLES

TABLE 3

| FR Size | Dilator OD (in) | Valve Hole Ø (in) | Valve Chamber Width (B) (in) | Chamber Height (in) | 1st Seal Thickness (in) | 2nd Seal Thickness (in) | Total Seal Thickness (1st + 2nd) (in) | % Hole Stretch |
|---|---|---|---|---|---|---|---|---|
| 7  | 0.092 | 0.070 | 0.215 | 0.070 | 0.020 | 0.035 | 0.055 | 31% |
| 8  | 0.111 | 0.070 | 0.215 | 0.070 | 0.020 | 0.035 | 0.055 | 59% |
| 9  | 0.118 | 0.090 | 0.270 | 0.070 | 0.020 | 0.035 | 0.055 | 31% |
| 10 | 0.137 | 0.090 | 0.270 | 0.070 | 0.020 | 0.035 | 0.055 | 52% |
| 11 | 0.144 | 0.090 | 0.270 | 0.070 | 0.020 | 0.035 | 0.055 | 60% |
| 12 | 0.158 | 0.120 | 0.310 | 0.070 | 0.020 | 0.035 | 0.055 | 32% |
| 13 | 0.171 | 0.120 | 0.310 | 0.070 | 0.020 | 0.035 | 0.055 | 43% |
| 14 | 0.189 | 0.120 | 0.310 | 0.070 | 0.020 | 0.035 | 0.055 | 58% |
| 15 | 0.197 | 0.150 | 0.320 | 0.070 | 0.020 | 0.035 | 0.055 | 31% |
| 16 | 0.208 | 0.150 | 0.320 | 0.070 | 0.020 | 0.035 | 0.055 | 39% |
| 7  | 0.092 | 0.070 | 0.215 | 0.050 | 0.040 | 0.035 | 0.055 | 31% |
| 8  | 0.111 | 0.070 | 0.215 | 0.050 | 0.040 | 0.035 | 0.055 | 59% |
| 9  | 0.118 | 0.090 | 0.270 | 0.050 | 0.040 | 0.035 | 0.055 | 31% |
| 10 | 0.137 | 0.090 | 0.270 | 0.050 | 0.040 | 0.035 | 0.055 | 52% |
| 11 | 0.144 | 0.090 | 0.270 | 0.050 | 0.040 | 0.035 | 0.055 | 60% |
| 12 | 0.158 | 0.120 | 0.310 | 0.050 | 0.040 | 0.035 | 0.055 | 32% |
| 13 | 0.171 | 0.120 | 0.310 | 0.050 | 0.040 | 0.035 | 0.055 | 43% |
| 14 | 0.189 | 0.120 | 0.310 | 0.050 | 0.040 | 0.035 | 0.055 | 58% |
| 15 | 0.197 | 0.150 | 0.320 | 0.050 | 0.040 | 0.035 | 0.055 | 31% |
| 16 | 0.208 | 0.150 | 0.320 | 0.050 | 0.040 | 0.035 | 0.055 | 39% |

FIGS. 14 and 15 illustrates another embodiment of an introducer assembly 300, including an introducer 310, such as a splittable or removable introducer, and a medical instrument 350 disposed therethrough. Examples of the medical instrument 350 include, but are not limited to, catheters, central venous catheters for a hemodialysis process, or dilators. The introducer 310 includes a passage therethrough that allows for the medical instrument 350 to be received therein, and allows for the introducer 310 to introduce the medical instrument 350 to be introduced into a patient. The introducer 310 further seals against the medical instrument 350.

Figure 16:
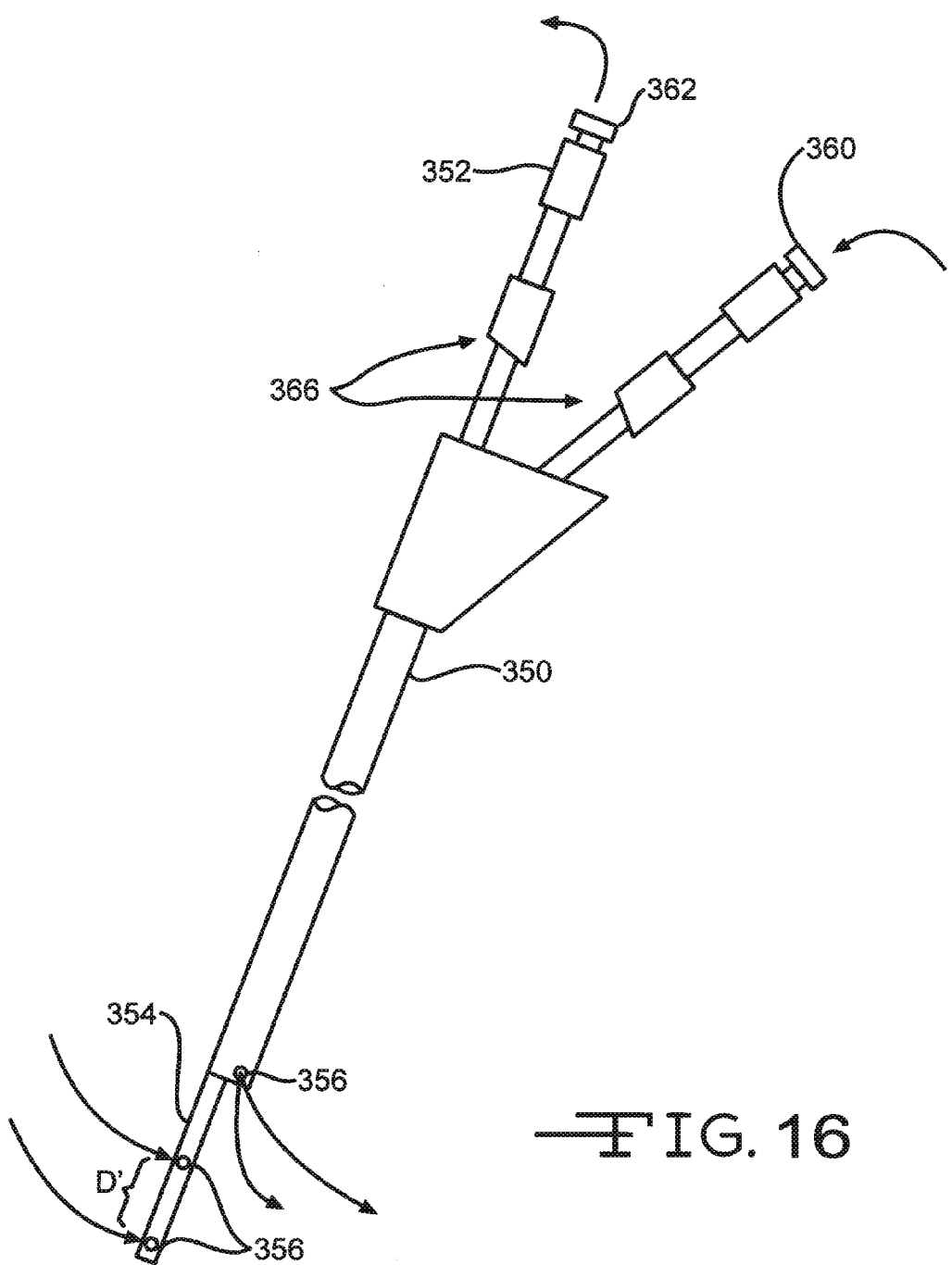
FIG. 16 illustrates a side elevational view of an example medical instrument for use with the introducing assembly.
Figure 20A:
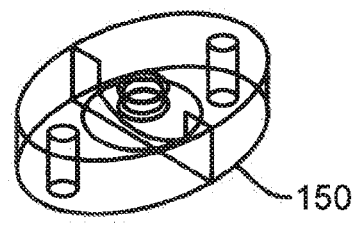
FIGS. 20A-20E illustrate various examples of a valve and slit configurations.
Figure 20B:
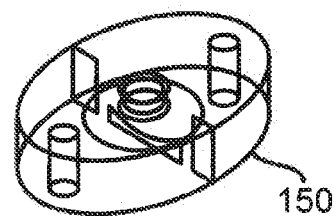
Figure 20C:
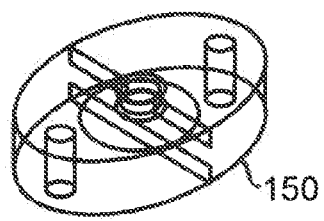
Figure 20D:
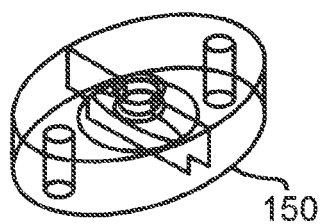
Figure 20E:
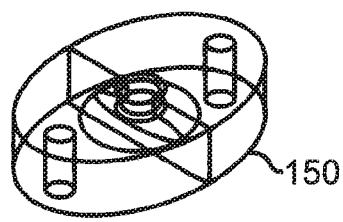

The medical instrument 350, shown in greater detail in FIG. 16, extends from a proximal end portion 352 to a distal end portion 354. In an example, the medical instrument 350 includes a number of openings 356, such as intake/discharge openings or flow holes that allow for fluids and/or gases to pass therethrough. In an example, the openings 356 are spaced apart a distance D' along a longitudinal axis of the medical instrument. In another example, the openings 356 are positioned near a distal end portion 354 of the medical instrument 350. In an example, the two or more openings 356 are spaced about 3 centimeters apart.

In another example, the medical instrument 350 includes an input 360 and an output 362 portion near the proximal end portion 352. For example, the output 362 allows for fluid such as blood to be removed from a body, and the input 360 allows for fluid such as blood to be returned or input into the body. The output 362 and the input 360 communicate with separate tubing lumens, in an option. In another option, each tubing lumen includes one or more openings 356. Further options include one or more clamp locations 366 which can be used to prevent air or blood from passing through the tubing unintentionally.

FIGS. 17, 18, and 19 illustrate greater details of the introducer 310, and illustrate the relative positions of the valves 314 and openings 356 on the medical instrument 350 as the medical instrument 350 is moved within the introducer 310. The introducer 310 is adapted to seal against the medical instrument 350, and also seals the passage 312 of the introducer 310 when the medical instrument 350 is not disposed within the introducer 310. The introducer 310 includes two or more valves 314 therein.

The two or more valves 314 are spaced along a longitudinal axis of the introducer 310, and are separated a distance D. The distance D, in an example, is at least is great, or in another example, is greater than distance D'. In an example, D is greater than 0.010 inches. In another example, D is less than about 2.0 inches. The two or more valves 314 define in part a chamber 320 therebetween. The valve spacing and/or the chamber volume is such that the openings 356 can be between the valves 314, and there is a limited opportunity for air to be introduced into the body via the introducer. For example, when the medical instrument 350 is disposed relative to the valves 314 as shown in FIG. 17, only the air between the valves 314 or in the chamber 320 can be potentially introduced into the patient. However, the volume of air contained between the two valves 314 or within the chamber 320 is significantly less than a volume of air that would be considered clinically significant as an air embolism.

The valves 314, in an example, are self-sealing membranes, such as a slitted membrane. In another example, the valves 314 are one or more members disposed adjacent to each other to form a valve. In an example, one or more of the valves 314 include multiple valves, such as the double valves discussed above. It should be noted that one, two, or more of the valves 314 can include any of the valves discussed above, or illustrated in the figures. The valves, in an example, provide a hemostatic seal at venous pressures of at least +/−12 mm Hg.

During use of the device, a method includes disposing an instrument through an introducer, for example, the introducer having the qualities and/or incorporating any of the seals or valves discussed above. For example, the introducer has a sheath extending from a sheath proximal end to a sheath distal end, and the sheath has a passage therethrough. The introducer further includes a valve assembly that is sealingly associated with the passage. The method further includes sealing a valve of the valve assembly against the instrument, where the valve includes at least a first seal on a second seal and optionally a chamber disposed between the first and second seals. The first seal may have one or more first properties which are different than the second seal which has one or more second properties. For example, the first and second seals have different thicknesses, and/or different hardnesses. The first and second seals may include one or more slits, which for example, allows for non-symmetrical instruments to be sealed therein. In another option, disposing an instrument includes disposing an instrument with two or more flow holes spaced apart a distance D'. The seals or valves are spaced apart from one another a distance greater than D'.

The method further includes disposing the instrument through the first and second seals, in the optional chamber. The method further includes separating the valve assembly and the introducer from around a cross-sectional perimeter of the instrument, for example, without damaging the instrument that is disposed therein. For example, suitable methods for splitting the valve assembly include splitting the sheath, for example, along a weakened section along the sheath from the tabs and removing the u-shaped valve from around the instrument, or removing the sheath along scored sections of the sheath.

Additional options for the method including providing a chamber with a side exit, and sealing the side exit with a portion of the valve. In one option, a crush ring is provided with the valve assembly to close off a portion of the chamber and providing a sealed chamber portion. In one option, the method includes compressing a crush ring and compressing it with a ramped portion of the valve from pressure of the housing.

Advantageously, the introducer assembly described above provides many benefits. For example, the introducer assembly allows for a removable introducer assembly to seal against very soft instruments such as soft tipped leads or soft and delicate instruments, or devices with relatively low column strength. Another benefit is that the introducer allows for passing up instruments through a seal with delicate features and/or tips through such sealing features, yet allowing for effective sealing against such devices. Examples of such delicate features include fasteners, electrodes, or coatings. Furthermore, the various features described above further allow for manufacturability of such a device and further allow for multiple seals having multiple different sealing properties to be incorporated with such a device. The multiple seals further allow for a first seal to seal against instruments disposed therethrough, and a second seal to seal a passage of the introducer when no instruments, or very small instruments are disposed therethrough. The introducer assembly further allows for removal of the introducer without disruption to the procedure or placement of the medical device such as a lead.

It is to be understood that the above description is intended to be illustrative, and not restrictive. Many other embodiments will be apparent to those of skill in the art upon reading and understanding the above description. It should be noted that embodiments or portions thereof discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. An introducer assembly comprising:
   a) a sheath extending from a sheath proximal end to a sheath distal end, the sheath having a passage there through; and
   b) a valve assembly sealingly associated with the sheath passage, the valve assembly comprising:
      i) a first valve comprising a first seal and a second seal with a first chamber disposed there between; and
      ii) a second valve comprising a third seal and a fourth seal with a second chamber disposed there between; and
   c) wherein the first and second valves are separate and independent valves spaced apart from each other by a valve distance.

2. The introducer of claim 1 wherein the first seal has a first sealing thickness and the second seal has a second sealing thickness.

3. The introducer of claim 2 wherein the first chamber is defined by a first chamber thickness, and at least one of the first sealing thickness and the second sealing thickness is lesser than the first chamber thickness.

4. The introducer of claim 2 wherein the first sealing thickness is different than the second sealing thickness.

5. The introducer of claim 1 wherein the third seal has third sealing thickness and the fourth seal has a fourth sealing thickness that is different than the third sealing thickness.

6. An introducer assembly comprising:
   a) a sheath extending from a sheath proximal end to a sheath distal end, the sheath having a passage there through;
   b) a valve assembly sealingly associated with the sheath passage, the valve assembly comprising:
      i) a first valve; and
      ii) a second valve; and
   c) wherein at least one of the first and second valves comprises a first seal having a first sealing thickness and a second seal having a second sealing thickness with a first chamber disposed between the first and second seals; and
   c) wherein the first and second valves are separate and independent valves spaced apart from each other by a valve distance.

7. The introducer of claim 6 wherein the first chamber is defined by a first chamber thickness, and at least one of the first sealing thickness and the second sealing thickness is lesser than the first chamber thickness.

8. The introducer of claim 6 wherein the first seal has a first hole defined by a first hole diameter and the first sealing thickness.

9. The introducer of claim 8 wherein the first hole has a stretch of about 30-60% of its original size.

* * * * *